United States Patent
Vierk

(10) Patent No.: US 7,651,508 B2
(45) Date of Patent: Jan. 26, 2010

(54) DIAMABRASION SYSTEM

(76) Inventor: Dan A. Vierk, 45350 Soldier's Home Rd., West Lafayette, IN (US) 47906

( * ) Notice: Subject to any disclaimer, the term of this patent is extended or adjusted under 35 U.S.C. 154(b) by 1181 days.

(21) Appl. No.: 10/930,473

(22) Filed: Aug. 31, 2004

(65) Prior Publication Data

US 2006/0047288 A1    Mar. 2, 2006

(51) Int. Cl.
A61B 17/50    (2006.01)

(52) U.S. Cl. ........................ 606/131; 206/210

(58) Field of Classification Search ............. 606/36, 606/131–133; 206/208–210
See application file for complete search history.

(56) References Cited

U.S. PATENT DOCUMENTS

| | | | |
|---|---|---|---|
| 2,701,559 A | 2/1955 | Cooper | |
| 2,712,823 A | 7/1955 | Kurtin | |
| 2,867,214 A | 1/1959 | Wilson | |
| 2,881,763 A | 4/1959 | Robbins | |
| 2,921,585 A | 1/1960 | Schumann | |
| 3,964,312 A | 6/1976 | Karden | |
| 4,378,804 A | 4/1983 | Cortese | |
| 5,012,797 A | 5/1991 | Liang | |
| 5,037,431 A | 8/1991 | Summers | |
| 5,037,432 A | 8/1991 | Mlinari | |
| 5,100,412 A | 3/1992 | Rosso | |
| 5,800,446 A | 9/1998 | Banuchi | |
| 5,971,999 A | 10/1999 | Naldni | |
| 6,039,745 A * | 3/2000 | Di Fiore et al. | 606/131 |
| 6,241,739 B1 * | 6/2001 | Waldron | 606/131 |
| 6,277,128 B1 * | 8/2001 | Muldner | 606/133 |
| 6,299,620 B1 * | 10/2001 | Shadduck et al. | 606/131 |
| 6,432,114 B1 | 8/2002 | Rosso | |
| 6,500,183 B1 | 12/2002 | Waldron | |
| 6,582,442 B2 | 6/2003 | Simon | |
| 6,592,595 B1 | 7/2003 | Mallet | |
| 6,629,983 B1 * | 10/2003 | Ignon | 606/131 |
| 6,695,853 B2 * | 2/2004 | Karasiuk | 606/131 |
| 6,911,031 B2 * | 6/2005 | Muldner | 606/131 |
| 7,070,488 B2 * | 7/2006 | Suissa et al. | 451/87 |
| 2003/0093089 A1 * | 5/2003 | Greenberg | 606/131 |

FOREIGN PATENT DOCUMENTS

WO    WO2004/037098    *    5/2004

* cited by examiner

Primary Examiner—Anhtuan T Nguyen
Assistant Examiner—Kathleen Sonnett
(74) Attorney, Agent, or Firm—Frank D. Lachenmaier

(57) ABSTRACT

The DiamAbrasion System is a system for removing portions of the outer layers of skin comprising a source of vacuum; abrasive tipped tools; a tube with an internal lumen connecting the vacuum source and the center of the abrasive tipped tools whereby the vacuum functions to clean the skin of exfoliated cells and collect them for disposal to an inline filter. The inventive difference between the DiamAbrasion System and the prior art is in the design of the pick-up-treatment head of the apparatus. The prior art utilizes the low pressure section of the tip to suck the skin against the abrasive surface and to evacuate the abraded cells. The DiamAbrasion System has vent grooves across the abrasive surface of the distal ends of the tool tips to keep the vacuum from pulling the skin into the head. This is particularly important as many of the users of this device are elderly and their skin is not resilient and tends to bunch up in front of the tip. The clean and dispose function is also greatly enhanced as the vent grooves allow a constant flow of air up the lumen to rapidly carry away the dislodged cells.

8 Claims, 6 Drawing Sheets

DIAMABRASION SYSTEM

BACKGROUND

1. Field of Invention

Figure 1:
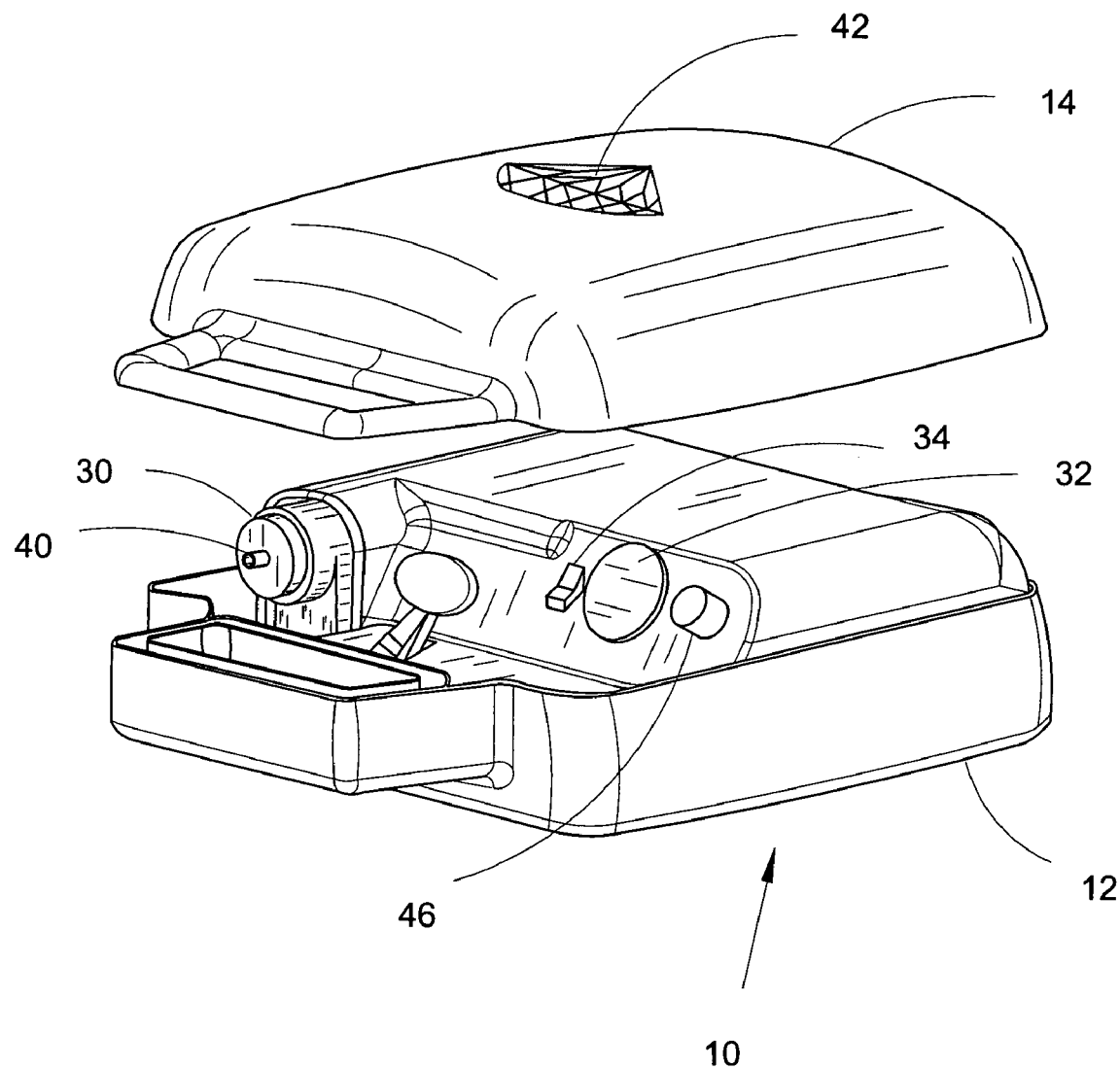

This invention generally relates to a self-contained device for removing outer layers of skin.

More particularly comprising a housing or a portable case; a vacuum source; a disposable filter; a vented abrasive treatment tipped tool; and a tube that has an internal lumen connecting the tool to the vacuum source providing the means to carry the abraded cells back to the filter.

2. Prior Art

Grinding and sanding machines with vacuum sources to remove the abraded material and accompanying dust are represented by U.S. Pat. No. 3,964,312.

Abrasive surfaces or rotating brushes or sanding discs have been used to remove layers of human skin (U.S. Pat. No. 6,500,183, U.S. Pat. No. 2,712,823, U.S. Pat. No. 2,867,214, U.S. Pat. No. 2,921,585, and U.S. Pat. No. 2,881,763 U.S. Pat. No. 2,701,559).

Blasting the skin surface with various reducing media and conveying mediums is illustrated in U.S. Pat. No. 5,037,432, U.S. Pat. No. 5,100,412, U.S. Pat. No. 5,971,999, U.S. Pat. No. 6,432,114, U.S. Pat. No. 6,582,442, U.S. Pat. No. 6,592,595, and U.S. Pat. No. 6,695,853.

Water jets (U.S. Pat. No. 5,037,431), ultrasonic tools (U.S. Pat. No. 5,012,797) and pulsating vacuum combined with a rotating brush (U.S. Pat. No. 4,378,804) have also been used to remove diseased or damaged soft tissue without injuring the underlying or adjacent healthy tissue. A glove with abrasive material on several fingers and the palm (U.S. Pat. No. 5,800,446) has also been disclosed.

U.S. Pat. No. 6,241,739 to Waldron discloses a treatment tool and tissue collection system for removal of outer layers of skin and a method of using same comprising an abrasive tipped tool mounted on the end of a vacuum tube. The vacuum is used to remove the abraded cells and it is also used to suck the skin against the abrasive tip with vacuum control to adjust the depth of cut.

SUMMARY

The DiamAbrasion System is a system for removing portions of the outer layers of skin comprising 1) a source of vacuum; 2) a tube with an internal lumen; and an abrasive tipped tool and 3) a vacuum functioning to clean the skin of exfoliated cells and collect them for disposal. The inventive difference between the DiamAbrasion System and the prior art is in the design of the pick-up-treatment head of the apparatus. The prior art utilizes the low pressure section of the tip to suck the skin against the abrasive surface and to evacuate the abraded cells. The DiamAbrasion System in fact has vent grooves across the abrasive surface of the distal ends of the tool tips to keep the vacuum from pulling the skin into the head. This is particularly important as many of the users of this device are elderly and their skin is not resilient and tends to bunch up in front of the tip like a throw rug in front of a vacuum sweeper. The clean and dispose function is also greatly enhanced as the vent grooves allow a free flow of air up the lumen to rapidly carry away the dislodged cells.

The objectives of the DiamAbrasion System are: to provide an apparatus for and method of removing the outer layer of the skin without any disposable consumables; to provide an apparatus for and method of removing the outer layer of the skin with no particulate to manage; to provide an apparatus for and method of removing the outer layer of the skin wherein eye protection for either the operator or the patient is not required; to provide an apparatus for and method of removing the outer layer of the skin that does not cause the skin to bunch up in front of the abrasion tool; to provide an apparatus for and method of removing the outer layer of the skin that uses diamond crystals bonded to the distal end of the tools; to provide an apparatus for and method of removing the outer layer of the skin that is portable, compact and weighs less than 25 lbs; to provide an apparatus for and method of removing the outer layer of the skin wherein the working tool handles are ergonometric in design for ease of use even if the user has diminished dexterity; to provide an apparatus for and method of removing the outer layer of the skin that generates minimal trauma due to noise levels and finally to provide a commercial apparatus for and method of removing the outer layer of the skin that utilizes metal tools that can be sterilized and re-used for different patients.

BRIEF SUMMARY OF INVENTION

The DiamAbrasion System is comprised of a vacuum source, a tube with an internal lumen, and several tools with vents across the abrasive ends and various grits of abrasive and shapes for abrading different parts of the body wherein the tube connects the tools to the vacuum source for carrying away the exfoliated cells. There are two embodiments of this invention that will be described with the assistance of the following drawings. The first embodiment is a personal, portable unit with its own carrying case. The second embodiment utilizes all the same principles but is a larger portable installation designed for commercial use with sterilizable metal tools.

DRAWINGS

Figure 2:
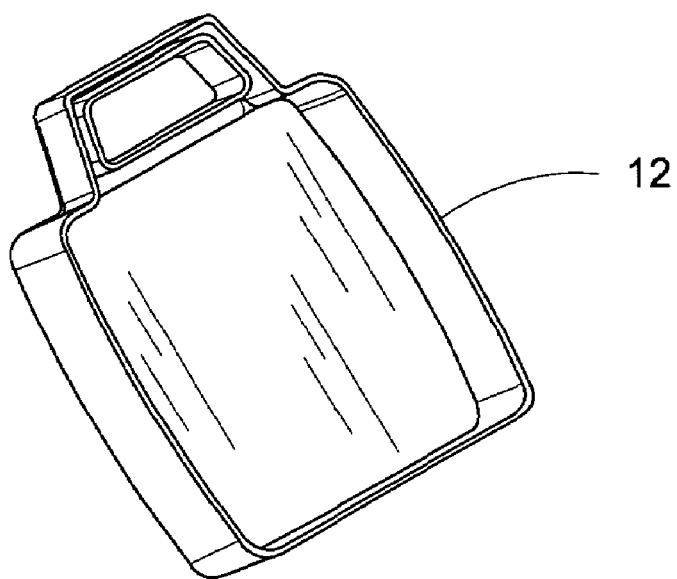
Figure 3:
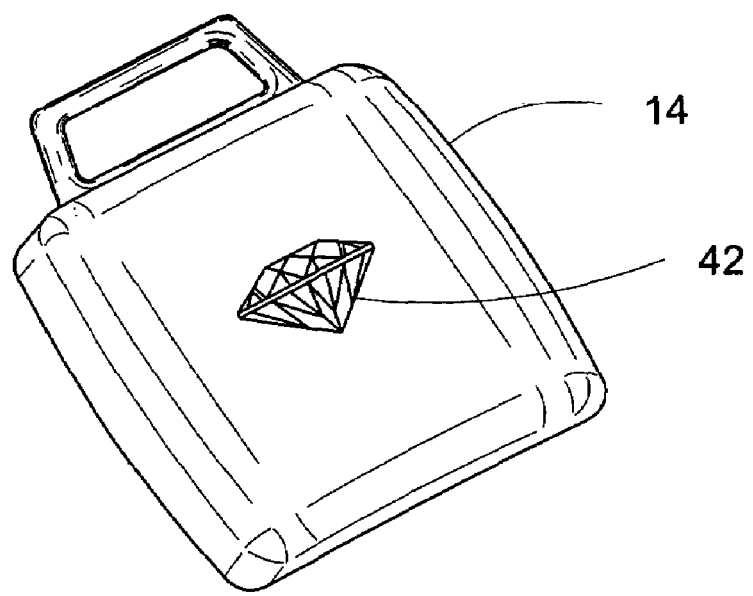
Figure 4:
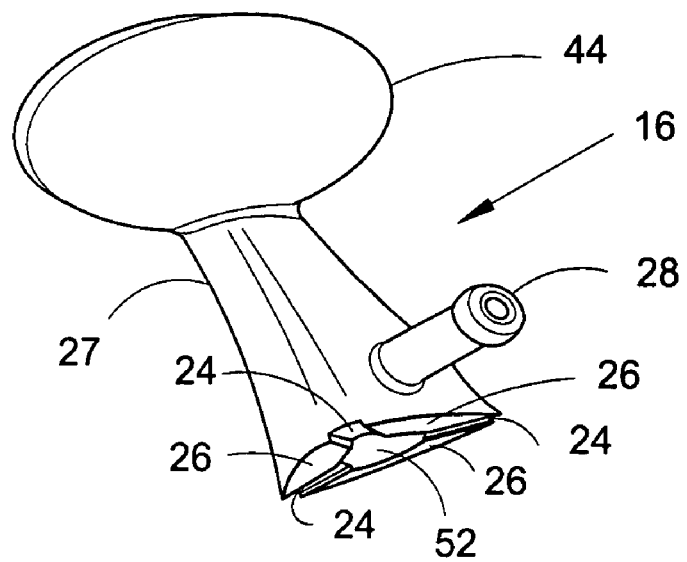
Figure 5:
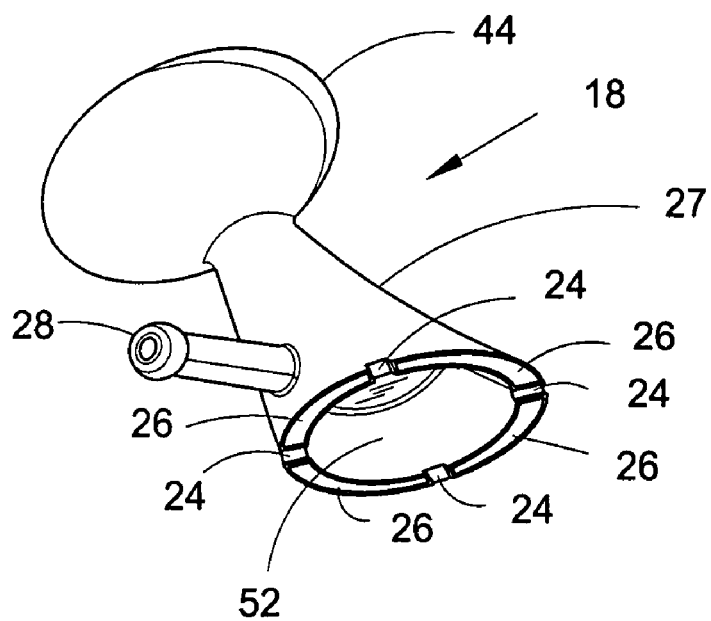
Figure 6:
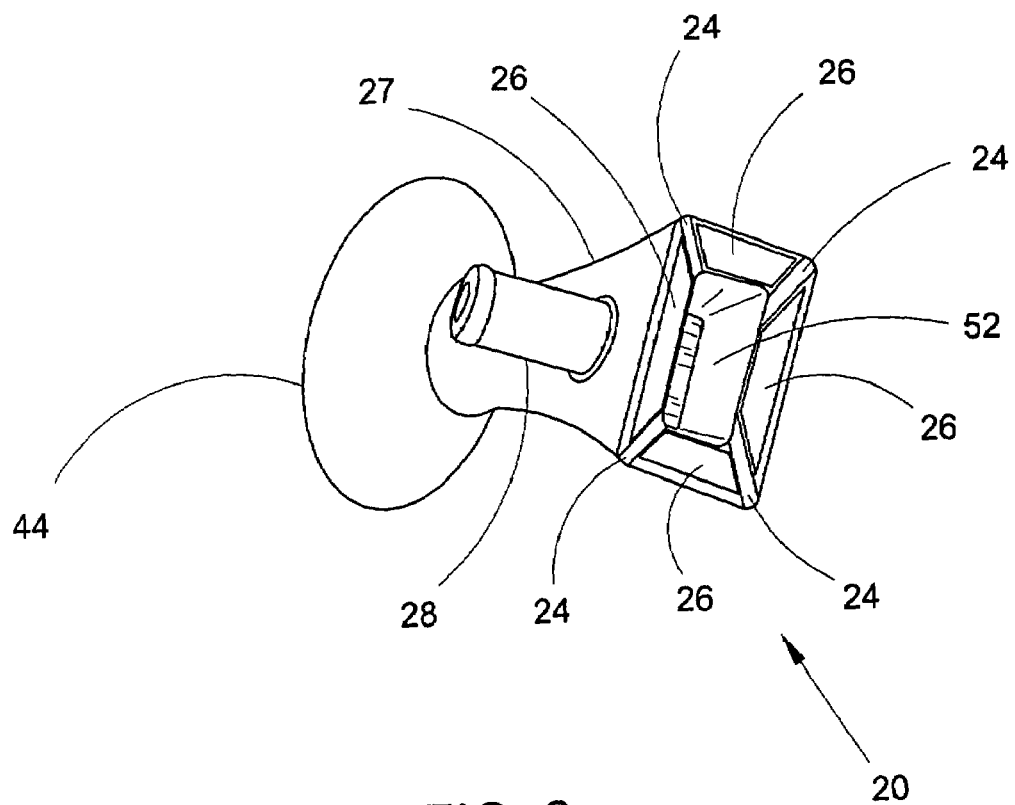
Figure 7:
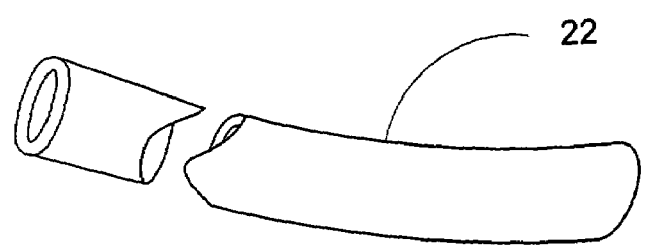
Figure 8:
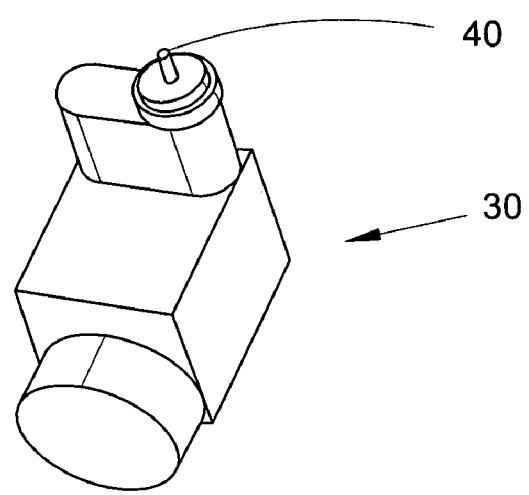
Figure 9:
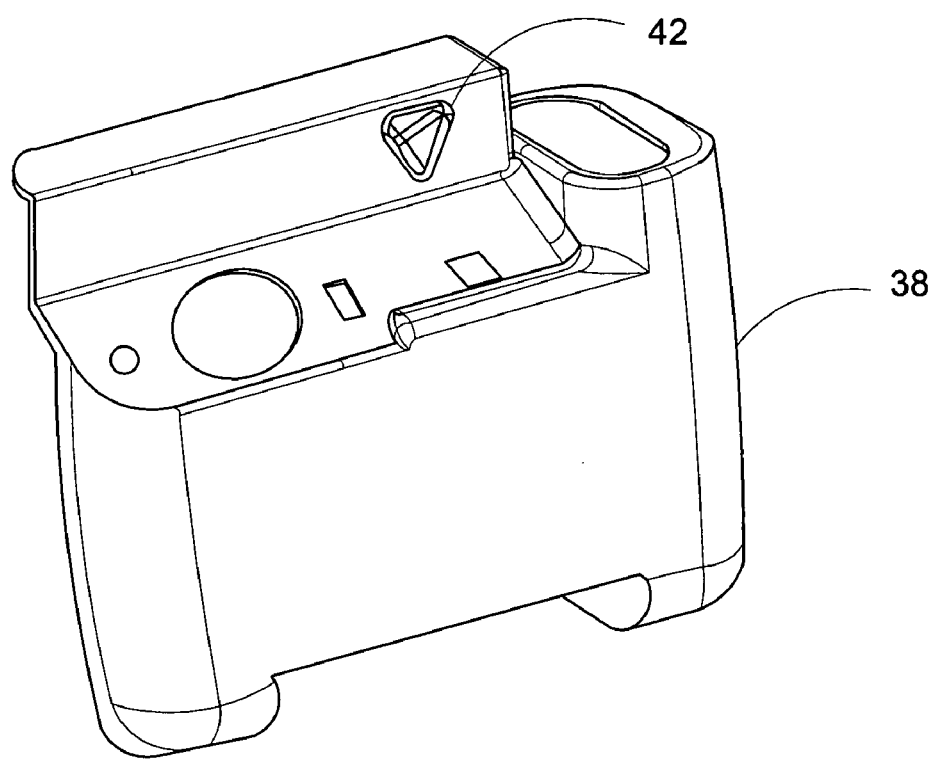
Figure 10:
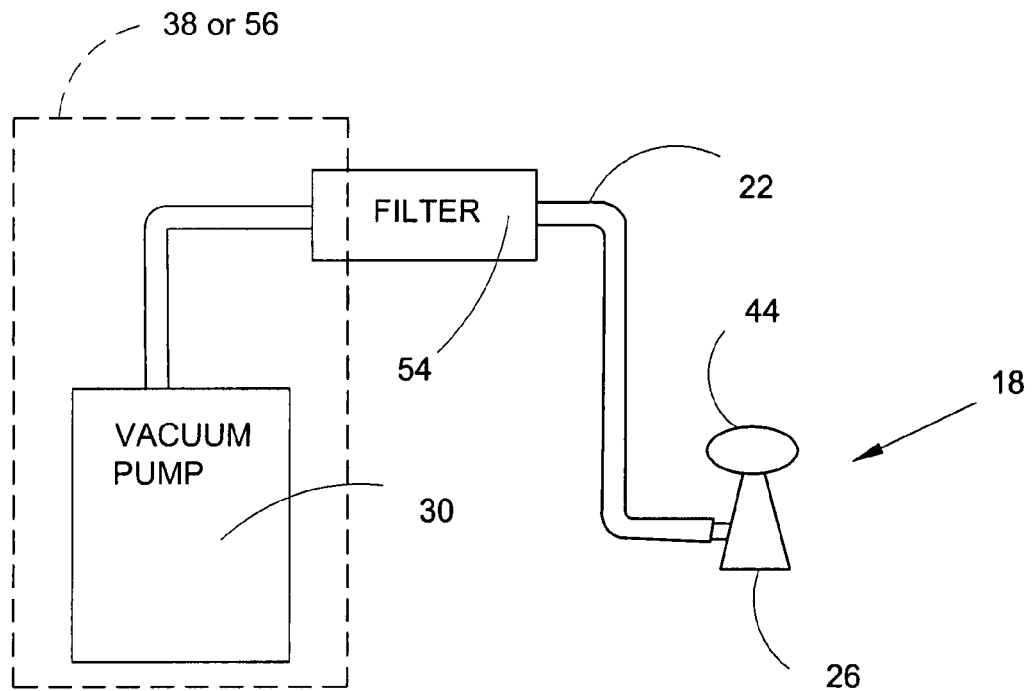
Figure 11:
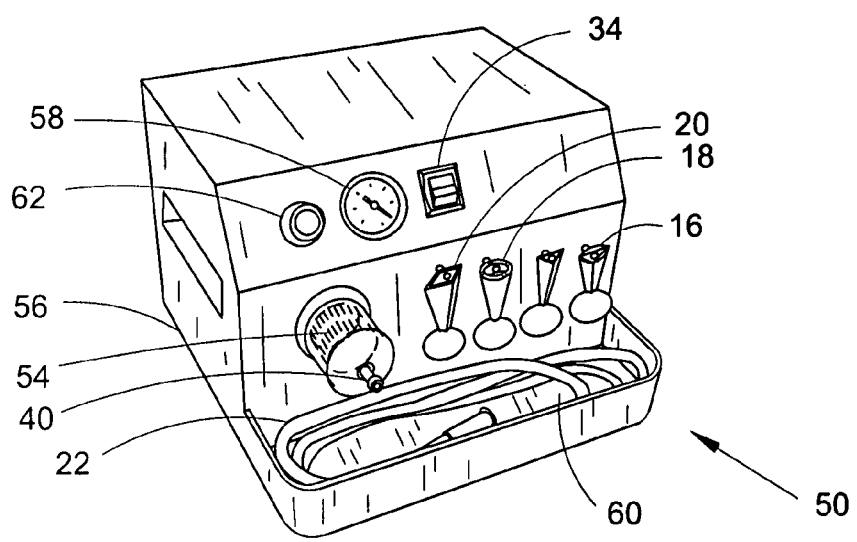

In order that the invention may be more fully understood it will now be described by way of example, with reference to the accompanying drawings in which FIG. 1 is an exploded isometric view of the personal system showing the case with the assembled unit FIG. 2 is an isometric view showing the base of the carrying case FIG. 3 is an isometric view showing the cover of the carrying case FIG. 4 is an isometric view showing the face tool FIG. 5 is an isometric view showing the foot tool FIG. 6 is an isometric view showing the body tool FIG. 7 is an isometric view showing the vacuum tube or lumen FIG. 8 is an isometric view showing the vacuum pump FIG. 9 is an isometric view showing the personal system housing FIG. 10 is a block diagram showing the System FIG. 11 is an isometric view showing the commercial system

REFERENCE NUMERALS

10—Personal Diamabrasion System
12—carrying case base
14—carrying case cover
16—DiamAbrader tool face tool
18—DiamAbrader tool foot tool
20—DiamAbrader tool body tool
22—vacuum tube or lumen
24—vent grooves 26—DiamAbrader tool diamond crystal abrasive/working surface
27—DiamAbrader tool body
28—tool vacuum port
30—vacuum pump
32—mirror
34—on-off switch
36—tool retaining slot
38—personal system housing
40—pump vacuum port
42—logo
44—DiamAbrader tool ergonomic handle
46—on light
48—carrying case handle
50—Commercial Diamabrasion System
52—internal channel
54—filter assembly
56—commercial system housing
58—Vacuum gage
60—tray
62—vacuum adjust

DETAILED DESCRIPTION

In order that the invention may be more fully understood, it will now be described by way of example with reference to the accompanying drawings which represent and illustrate two embodiments, Personal Diamabrasion System 10 and Commercial Diamabrasion System 50.

The first embodiment, Personal Diamabrasion System 10, shown in FIG. 1, is lightweight, less than approximately 25 lbs, portable with its own briefcase sized carrying case base 12 and cover 14. The three tools included in Personal Diamabrasion System 10 are face tool 16, foot tool 18 and body tool 20 shown in FIGS. 4, 5 and 6 respectively. Their working surfaces 26 have vent grooves 24 cut across their faces from the outside periphery to internal channel 52 and it connects through tool vacuum port 28 to the vacuum lumen or tube 22 which connects to vacuum port 40 on vacuum source 30. The tools for Personal Diamabrasion System 10 are typically molded from an engineering grade of injection thermoplastic. The three tools 16, 18 and 20 as described in FIGS. 4, 5 and 6, are shown as exemplary of the various end effects and shapes that maybe used but are not intended to limit the shapes that are covered in this application.

The second embodiment, Commercial Diamabrasion System 50, is a stationary system meant for commercial use. It includes all of the same elements as Personal Diamabrasion System 10 with additional features for commercial use. Commercial Diamabrasion System 50 utilizes tools with similar dimensions and operating characteristics as Personal Diamabrasion System 10 but its tools are constructed from a material such as stainless steel that can be repeatedly sterilized for use with different patients. Lumens 22 for Commercial Diamabrasion System 50 are made from inexpensive and disposable plastic tubing that carries exfoliated cells back into filter 54 that also has a disposable element for each new client. Commercial DiamAbrasion System 50 has mounting holes in its front face that tool vacuum ports 28 protrude into for storage and retention of the tools as shown in FIG. 11. It also has a front tray 60 for storing spare lumens 22.

Both embodiments provide microderm abrasion without external media flowing across the soft tissue being treated. They both utilize various size and shape tools that have diamond particle abrasives/working surfaces 26 and their working surfaces 26 have vents 24 cut across them to an internal channel 52.

Ergonomically designed egg shaped handles 44 allow for easy manipulation of abrasive working surface 26 across the skin even if the user suffers from limited physical dexterity. Vents 24 break the vacuum between working surfaces 26 of tools 16, 18 and 20 and the skin allowing the tools to move smoothly across the skin even if the skin being treated has lost its resiliency. When the diamond particles are rubbed across the skin, the cells on the outer layer are exfoliated and cleaned from the skin surface by vacuum from a vacuum source such as pump 30 through lumen 22.

Turning to FIG. 1, the units that make up Diamabrasion System 10 are shown in case 12 with cover 14 open. FIG. 1 shows pump 30 installed in housing 38 with mirror 32 attached and on-off switch 34 mounted and body tool 20 in storage slot 36.

FIG. 2 shows carrying case base 12 with handle 48 and FIG. 3 shows carrying case cover 14.

FIGS. 4, 5 and 6 disclose the designs of three different abrasive tipped tools 16, 18 and 20 and FIG. 7 shows the lumen as a flexible tube. FIG. 8 is a schematic representation of vacuum pump 30 and FIG. 9 shows the housing for the components of Personal Diamabrasion System 10.

FIG. 11 shows Commercial DiamAbrasion System 50 with four DiamAbrader tools hanging from their tool vacuum ports 28 on the face of housing 56. It also shows lumen 22 stored in front tray 60, filter assembly 54 and pump vacuum port 40 protruding from the front face of housing 56 and on-off switch 34, vacuum gage 58 and vacuum adjustment 62 conveniently mounted on its upwardly angled top of its front surface.

Operation:

Block diagram in FIG. 10 shows the operation of Personal Diamabrasion System 10 and Commercial Diamabrasion System 50.

The appropriate tool is selected for the body part to be treated and the distal end of flexible tube or lumen 22 is stretched over tool vacuum port 28 of the selected tool. The proximal end of lumen 22 is stretched over pump vacuum port 40 which connects to filter 54. An internal line then connects the base of filter 54 to vacuum pump or source 30. Vacuum pump 30 is turned on and the diamond crystal abrasive/working surface 26 of the selected hand tool is moved across the skin section to be treated abrading the dead or damaged cells and freeing them to be vacuumed back to filter 54. Vents 24 cut across working surface 26 allow the selected hand tool to move smoothly over the skin to be treated and enough air moving up lumen 22 to efficiently collect the abraded cells and deposit them in filter 54.

While the DiamAbrasion System has been described with reference to two preferred embodiments thereof, it will be appreciated by those skilled in the art that variations in form, detail, and composition may be made without departing from the scope of this invention as defined by the accompanying claims.

The invention claimed is:

1. An apparatus for removing dead and damaged cells from the outer layer of the skin comprising:
    a housing;
    a source of vacuum;
    DiamAbrader tools with ergonomically designed egg shaped handles, working surfaces with diamond particles bonded to said working surfaces, bodies connecting said handles to said working surfaces, external vacuum ports extending outward from said bodies and connected to an internal channel in the center of said bodies that leads to the centers of said working surfaces and vent grooves cut across said working surfaces connecting said internal channel to ambient air; and a flexible lumen connecting said vacuum source to said vacuum ports on said DiamAbrader tools, whereby air is drawn across the treated skin, pulling exfoliated cells toward said vacuum source.

2. The apparatus of claim 1 wherein the apparatus is housed in personal system housing that fits in a briefcase type carrying case for transportation or storage case and cover.

3. The apparatus of claim 2 wherein said vacuum source is a vacuum pump mounted in said carrying case.

4. The apparatus of claim 1 wherein the apparatus is housed in a stationary commercial housing.

5. The apparatus of claim 1 wherein said DiamAbrader tool working surfaces have a grit of between approximately 100-250 microns.

6. The apparatus of claim 1 wherein said DiamAbrader tool bodies are molded from an injection grade thermoplastic.

7. The apparatus of claim 1 wherein said DiamAbrader tool housings are made from stainless steel, whereby the DiamAbrader tools will withstand numerous sterilizations.

8. The apparatus of claim 1 further including a filter system interposed between said flexible lumen and said vacuum source that includes readily changeable disposable filter inserts.

* * * * *